US009358000B2

(12) United States Patent
Cichocki, Jr. et al.

(10) Patent No.: US 9,358,000 B2
(45) Date of Patent: *Jun. 7, 2016

(54) TUNGSTEN ALLOY SUTURE NEEDLES

(75) Inventors: Frank R. Cichocki, Jr., Easton, PA (US); Eugene D. Reynolds, Avon by the Sea, NJ (US); Robert E. Maurer, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 1826 days.

This patent is subject to a terminal disclaimer.

(21) Appl. No.: 11/611,353

(22) Filed: Dec. 15, 2006

(65) Prior Publication Data

US 2008/0147117 A1    Jun. 19, 2008

(51) Int. Cl.
*A61B 17/06* (2006.01)
*B21G 1/08* (2006.01)
*C22C 27/04* (2006.01)
*C22F 1/18* (2006.01)
*A61B 17/00* (2006.01)

(52) U.S. Cl.
CPC ............ *A61B 17/06066* (2013.01); *B21G 1/08* (2013.01); *C22C 27/04* (2013.01); *C22F 1/18* (2013.01); *A61B 2017/00526* (2013.01)

(58) Field of Classification Search
CPC ............... A61B 17/06066; A61B 2017/00526; C22F 1/18; B21G 1/08; C22C 27/04
USPC .......................................... 148/673; 606/223
See application file for complete search history.

(56) References Cited

U.S. PATENT DOCUMENTS

| 2,666,721 | A | 1/1954 | Bechtold et al. |
|---|---|---|---|
| 3,038,475 | A | 6/1962 | Orcutt |
| 3,236,699 | A | 2/1966 | Pugh |
| 3,238,942 | A | 3/1966 | Lincoff |
| 3,637,374 | A | 1/1972 | Holzi |
| 3,686,041 | A | 8/1972 | Lee |
| 4,501,312 | A | 2/1985 | Matsutani |
| 4,602,636 | A | 7/1986 | Noiles |
| 4,799,484 | A | 1/1989 | Smith et al. |
| 4,905,695 | A | 3/1990 | Bendel et al. |
| 4,959,068 | A | 9/1990 | Bendel et al. |
| 4,968,362 | A | 11/1990 | Prasad |
| 5,026,520 | A | 6/1991 | Bhowal et al. |
| 5,231,771 | A | 8/1993 | Samsel |
| 5,411,613 | A | 5/1995 | Rizk et al. |
| 5,415,707 | A | 5/1995 | Bendel et al. |
| 5,533,982 | A | 7/1996 | Rizk et al. |
| 5,649,961 | A | 7/1997 | McGregor et al. |
| 5,683,415 | A | 11/1997 | Brunken |
| 6,077,369 | A | 6/2000 | Kusano |
| 6,592,559 | B1 | 7/2003 | Pakter et al. |
| 7,001,472 | B2 | 2/2006 | Collier et al. |
| 7,014,722 | B1 | 3/2006 | Arimoto et al. |
| 7,063,716 | B2 | 6/2006 | Cunningham |
| 2001/0001401 | A1 | 5/2001 | Segal |
| 2005/0096698 | A1 | 5/2005 | Lederman |
| 2006/0058843 | A1 | 3/2006 | Mashiko et al. |

FOREIGN PATENT DOCUMENTS

| EP | 615726 | A1 | 9/1994 |
|---|---|---|---|
| EP | 646352 | A1 | 4/1995 |
| EP | 646352 | A1 | 4/1995 |
| EP | 646352 | B1 | 6/1998 |
| EP | 948933 | A1 | 10/1999 |
| EP | 948934 | A1 | 10/1999 |
| EP | 615726 | B1 | 1/2000 |
| EP | 1051538 | A1 | 11/2000 |
| EP | 1051538 | B1 | 10/2003 |
| EP | 948933 | B1 | 11/2003 |
| EP | 948934 | B1 | 11/2003 |
| JP | 3294449 | A | 12/1991 |
| JP | 4124205 | A | 4/1992 |

OTHER PUBLICATIONS

Mutoh et al., Effect of Rhenium Addition on Fracture Toughness of Tungsten at Elevated Temperatures, 1995, Journal of Materials Science, Chapman & Hall, 30, p. 770-775.*
Lillard, R. S. et al., "The Nature of Oxide Films on Tungsten in Acidic and Alkaline Solutions", J. Electrochem. Soc ., 1998.
Raffo, P. L., "Yielding and Fracture in Tungsten and Tungsten-Rhenium Alloys", NASA TN D-4567 (1968).

* cited by examiner

*Primary Examiner* — Roy King
*Assistant Examiner* — Caitlin Kiechle
(74) *Attorney, Agent, or Firm* — E. Richard Skula

(57) ABSTRACT

A method for making a curved tungsten alloy suture needle comprising the step of heating tungsten alloy needle blanks or a tungsten alloy suture needle to a temperature below the recrystallization temperature of the alloy. The tungsten alloy suture needles described herein have a desirable combination of stiffness, strength, ductility, and surface color.

12 Claims, 2 Drawing Sheets

TUNGSTEN ALLOY SUTURE NEEDLES

FIELD OF THE INVENTION

The present invention relates to suture needles, and in particular to tungsten alloy suture needles having a desirable combination of stiffness, strength and ductility. More specifically, the present invention relates to heat treated tungsten alloy suture needles that exhibit superior bending stiffness properties.

BACKGROUND OF THE INVENTION

Certain surgeries, particularly coronary artery bypass surgery, necessarily involve the use of suture needles of small diameter having exceedingly high bending stiffness and strength. In particular, surgery of this type requires that the suture needle's path be closely controlled. If the needle flexes excessively as it enters the tissue or as it pierces the inner surface of e.g., a blood vessel before re-emerging, improper placement of the needle and serious trauma to the tissue and the patient can occur. In use, suture needles are subjected to substantial stressing forces, since the force used to drive the needle into and through tissue (e.g., a blood vessel and the like) needs to be sufficient to overcome frictional drag through the tissue. These forces resisting needle penetration are commonly exacerbated in patients undergoing cardiovascular surgery, who exhibit calcified or toughened tissue due to coronary artery disease. In these procedures, the suture needle must be able to pass through not only the blood vessel, but also any hard calcified tissue that may be located along the periphery of the blood vessel lumen. A compliant needle will deflect elastically during tissue penetration resulting in a loss of placement control. As such, it is preferable that the needle should have a relatively high bending stiffness, that is, a low tendency to flex and high tendency to retain its configuration when subjected to a deforming force. Hence, stiffness in bending is an essential property for the handling and performance of suture needles. A stiff needle resists elastic deflection and can thus be directed as intended to provide a high level of control.

ASTM standard F1840-98a (Reapproved 2004) provides standard terminology for surgical suture needles and ASTM standard F1874-98 (Reapproved 2004) provides details of a standard test method for bend testing of needles used in surgical sutures. Both ASTM standards are incorporated herein by reference. Two different measures for the strength of surgical suture needles are used, namely, yield bend moment, which is the amount of moment required to initiate plastic deformation during a bend test, and maximum bend moment, which is the greatest moment applied to a needle during a bend test. This later value of maximum bend moment is typically measured at a point where the needle has undergone substantial plastic deformation and is generally higher than the yield bend moment or point at which plastic deformation initiates. The point of deflection at which plastic deformation initiates, or more formally according to ASTM standards, the angle at which the yield bend moment occurs, is referred to as the yield bend angle.

Both needle bending strength and needle bending stiffness influence handling characteristics, as well as penetration performance and efficacy of the suture needle. It is important to note that in almost all circumstances, the suture needle should be used in applications where the yield bend moment is not exceeded, since above this value, the needle will bend plastically, losing its original shape, and will no longer function as intended. It is thus apparent that a desirable characteristic of a suture needle is a high yield bend moment, which is a manifestation of the bending strength of the suture needle. Below the yield bend moment, the resistance of bending of the suture needle is best characterized by the needle bending stiffness. Needle bending stiffness is a critical measure of the resistance to elastic, or recoverable bending of the suture needle before needle deflection reaches the yield bend angle and can be calculated as the yield bend moment divided by the yield bend angle. If a straight or curved suture needle has a low value of bending stiffness, substantial bending of the needle will occur for a given bend moment, whereas if a straight or curved suture needle exhibits a high bending stiffness value, relatively little elastic bending of the needle will occur for a given bend moment. Surgeons will tend to perceive a high degree of elastic bending as a loss of control or as a poor penetration performance since the needle point is not translating directly with the motion of their hands. As such, needle bending stiffness may be recognized as a quintessential measure of needle performance in most surgical applications.

Hence, the desirable bend properties for a suture needle are high bending stiffness, as well as bending strength manifested as high yield bend moment and ductility, in order to penetrate tissue which is being sutured without undue flexing, plastic bending, or breaking during a surgical procedure.

The needle should also not be brittle; if any portion of the needle is too brittle it may break during use if too much force is applied. The needle should instead be ductile, which is the ability to bend without breaking. Curved suture needles are commonly bent through a bend angle of 90 degrees and then manually reshaped to their original curvature to assess ductility. Those skilled in the art of needle making will recognize this procedure as the reshaping process and will further recognize that the higher the number of reshape processes that a needle can withstand without breaking the more ductile it is.

U.S. Pat. No. 5,415,707 describes tungsten alloy surgical needles that exhibit high tensile yield strength in excess of 250,000 psi, high tensile modulus of elasticity or stiffness in excess of $45 \times 10^6$ psi, and high ductility. The needles described therein preferably comprise about 3 to about 6 weight percent of rhenium, rhodium and/or iridium. Data presented in U.S. Pat. No. 5,415,707 was derived from straight uncurved needles.

As described in U.S. Pat. No. 5,415,707, tungsten alloys have exceptionally high stiffness along with other desirable physical properties. Tungsten alloys derive their strength from their high dislocation density and the natural resistance to deformation that occurs via dislocation-dislocation interaction as a stress is applied. However, the exceptionally high stiffness of such tungsten alloys in wire and straight needle form does not necessarily translate to high bending stiffness when such alloys are used to make curved suture needles, since the curving process during needle manufacture imparts stresses that act to reduce the bending stiffness of the curved suture needle. It is believed that during the curving portion of the needle manufacture process, the dislocations in the tungsten alloy move to high energy locations within the microstructure, or locations where high strain field exist locally around the dislocations. When a moderate unbending force is applied to the curved suture needle, the dislocations in the high energy locations readily slip to positions of lower energy or lower local strain. The slip of these dislocations to lower energy positions manifests itself as limited plastic deformation, resulting in a relatively low stiffness in bending or low yield bend moment.

Thus, there is a need for tungsten alloy suture needles that exhibit high bending strength and high bending stiffness, particularly when the suture needle is a curved needle.

SUMMARY OF THE INVENTION

It has now been discovered that suture needles having a desirable combination of stiffness, strength and ductility can be formed from a tungsten alloy, by a method comprising the steps of (1) forming needle blanks comprising a tungsten alloy into a suture needle; and (2) heating said suture needle to a temperature below the recrystallization temperature of the alloy.

DETAILED DESCRIPTION OF THE INVENTION

Figure 1:
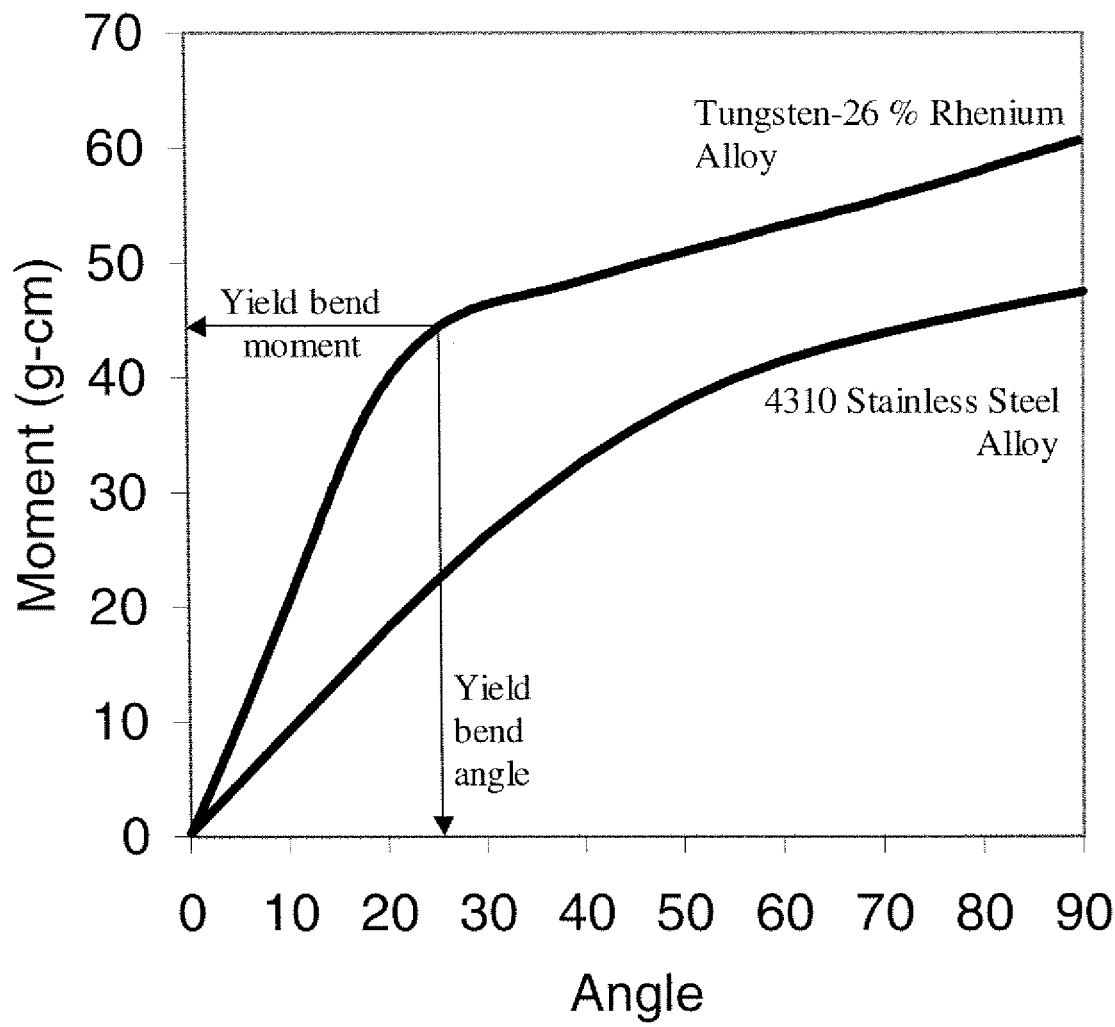
FIG. 1 is a graph comparing the bending performance of an 0.008" diameter curved suture needle produced from a tungsten 26% rhenium alloy to an equivalent suture needle produced from a curved 4310 stainless steel alloy.

The suture needles of the present invention are formed from an alloy of tungsten. The tungsten alloy may comprise one or more metals selected from the group consisting of rhenium, osmium, tantalum, or molybdenum. Preferably, the alloy is a tungsten-rhenium alloy, and has no more than trace amounts of other elements present. The metal other than tungsten may be present in an amount up to about 30 weight percent of the alloy, and more preferably is present in an amount ranging from about 20 to about 26 weight percent of the alloy.

The suture needle preferably has a diameter effective to permit satisfactory usage in fine surgery. Typically, the diameter will be less than about 60 mils (thousandths of an inch), preferably less than about 15 mils, down to about 1 mil, and preferably about 1.4 to about 12 mils. It will be recognized that the suture needle may have a circular body cross-section, and that the needle may also be of a non-circular cross-sectional shape such as triangular; trapezoidal; rectangular; hexagonal; elliptical; or rectangular wherein the opposed shorter ends of the rectangle are rounded into semicircles. By "diameter" herein is meant the square root of $(4 A/\pi)$ where A is the cross-sectional area. The needle may be provided with a "ribbon" shape with a single set of opposing flat sides, or a rectangular or "I-beam" shape, or with a cross-section which smoothly undergoes transition from the point to a circular cross-section, to a rectangular cross-section having rounded and then sharper corners, as described in U.S. Pat. No. 4,799,484.

The suture needle may be straight or curved, but the improvement in bending strength and stiffness is especially advantageous for curved needles. Preferably, the needle is curved through a radius of curvature, which need not be constant but is preferably constant. Thus, more preferred shapes of the needles of the present invention comprise sections of a circle, such as a quarter circle, three-eighths circle, half circle, or five-eighths of a circle.

Following the final drawing of the tungsten alloy wire to the final desired diameter, one end of the needle is given a point having the desired shape, the point being provided by any conventional technique such as grinding. Optionally, the body may be formed by pressing or grinding operations into the variety of shapes. The needle may then be given its desired curvature, typically by rolling around a mandrel of the desired radius of curvature. The opposite end of the needle is given an opening in its end, or other means by which the end of a suture can be attached to the needle by swaging or the like.

In order to impart improved bending strength and stiffness to the suture needle described herein, particularly after a curvature has been imparted to the needle, the curved needle is heated to a temperature below the recrystallization temperature of the tungsten alloy. It shall be noted that for purposes of this disclosure, recrystallization temperature is defined as any temperature in which the microstructure of the tungsten alloy suture needles may be changed via the formation of new grains. Preferably, the suture needle is heated to a temperature ranging from about 700 to about 1900° C. In one embodiment of the invention, the suture needle is heated to a temperature ranging from about 800 to about 1150° C. in an inert or reducing atmosphere for about 0.5 hours to impart bending stiffness to the surgical needle. Needles may also be attached to a tape or other conveyer material and passed transiently in the vicinity of a heat source. In this way the exposure time to elevated temperature would be limited, since it will be recognized that higher temperatures for shorter periods of time are effective to achieve the desired stiffening effect. Examples of an inert or reducing atmosphere include, but are not limited to, vacuum, argon gas, nitrogen gas, hydrogen gas, or gas mixtures thereof.

In an alternate embodiment, the suture needle is heated to a temperature ranging from about 350 to about 900° C. in an oxidizing atmosphere, in order to impart a robust adherent black, blue, or yellow oxide surface coating to the tungsten alloy suture needle described herein. For example, the suture needles and/or the needle blanks may be placed flat on a setter plate and introduced into a preheated furnace at a temperature between 350 and about 900° C. Alternatively, the needles may be placed in the furnace at room temperature as the furnace ramps up to the target temperature and then back down to room temperature. Needles may also be attached to a tape or other conveyer material and passed transiently in the vicinity of a heat source. Exposure time may range from seconds to several hours, depending upon the temperature. More preferably temperatures range from about 400 and about 600° C. for duration of about 0.25 to about 1 hour. Examples of an oxidizing atmosphere include, but are not limited to, oxygen-rich atmosphere, air, or a carbon dioxide/carbon monoxide gas mixture that decomposes or reacts with the tungsten alloy surface to form an oxide.

In another embodiment, the suture needle may first be heated to a temperature ranging from about 700 to about 1900° C. in an inert or reducing atmosphere, followed by heating to a temperature ranging from about 350 to about 900° C. in an oxidizing atmosphere, to impart improved bending stiffness and a robust adherent black, blue, or yellow surface coating to the tungsten alloy suture needles.

The needle may also be provided with a coating, for instance, a polymeric coating, in accordance with known techniques, if desired. The needle is then attached to the suture, packaged and sterilized, again in accordance with conventional techniques.

The suture needles of the present invention are characterized by a desirable combination of bending stiffness, strength and ductility. For the needles of the present invention, the wire tensile yield strength is generally at least about 250,000 ksi. A high wire tensile yield strength is useful as it indicates the ability of the needles of the present invention to withstand potentially deforming stresses without suffering permanent deformation.

The wire from which the needles of the present invention are made also exhibits uniquely high Young's modulus of elasticity, generally at least about 400 GPa. The high Young's modulus is desirable in that it reflects the potential for higher stiffness and the ability of the needles of the present invention to withstand potentially deforming stresses by retaining their shape, without undue flexing. However, in practice, as described above, a high Young's modulus of the wire alone does not directly translate into a high bending stiffness for a curved suture needle. Indeed to capitalize on the intrinsic material stiffness, a heat treatment is applied to the curved suture needles, as described above.

The properties of the suture needles of the present invention are illustrated in the following examples, which are provided for purposes of illustration and should not be interpreted as limiting in any way the scope of the claims appended hereto.

Example 1

A graph comparing the bending performance of a heat treated curved 0.008" diameter suture needle produced from a tungsten 26% rhenium alloy to an equivalent curved suture needle produced from a commercial 4310 stainless steel alloy used in the manufacture of suture needles is provided in FIG. 1. All tests were conducted according to ASTM standard F1874-98. The yield bend moment and yield bend angle are marked on the graph. The slope of the tungsten-rhenium alloy suture needle up to the yield bend moment represents bending stiffness and is markedly greater than that provided by the equivalent 4310 stainless steel alloy. The heat treatment applied to the tungsten alloy suture needle was conducted under an argon 2% hydrogen atmosphere at 1000° C. for 0.5 hrs.

Example 2

Figure 2:
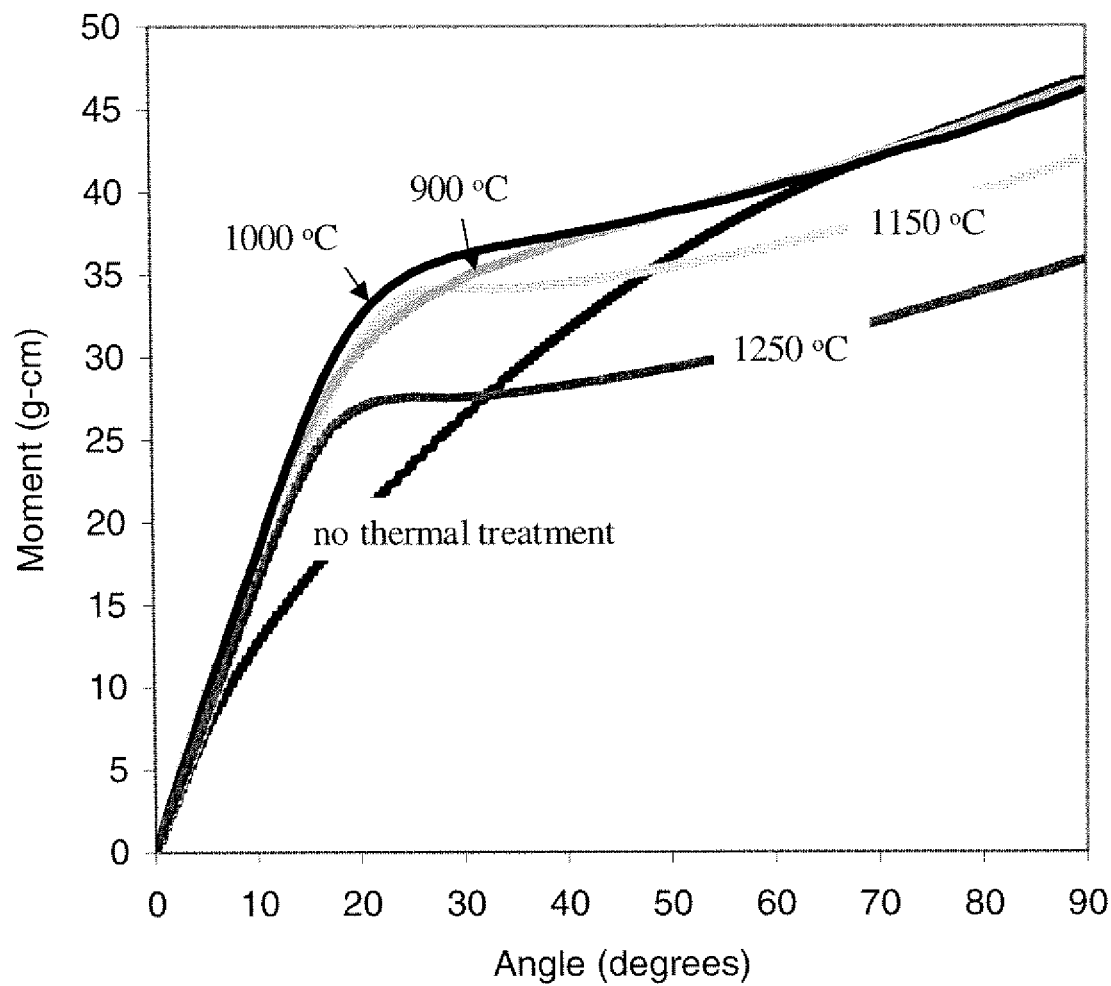
FIG. 2 is a graph showing the bending performance of tungsten 25.75% rhenium suture needles as a function of heat treatment temperature for a duration of 0.5 hour.

A graph comparing the bending performance of curved 0.008" diameter suture needles produced from a tungsten 25.75% rhenium alloy after thermal treatment for 0.5 hr over a range of temperature is shown in FIG. 2. Heat treatment was conducted under argon 2% hydrogen gas to maintain an inert non-oxidizing atmosphere. All tests were conducted according to ASTM standard F1874-98. A marked increase in bending stiffness occurs with the application of heat treatment. A maximum in bending stiffness is attained with a thermal treatment of 1000° C. for 0.5 hr. At temperatures above and below 1000° C. a decrease in the yield bend moment occurs.

It shall be recognized that similar results may be achieved with shorter duration thermal treatments at elevated temperatures and result in an upward shift for the optimal heat treatment temperature. Likewise, extended duration thermal treatments at lower temperatures may also be effective and result in a downward shift of the optimal treatment temperature.

What is claimed is:

1. A method for making a tungsten alloy suture needle comprising the steps of:
   forming needle blanks or suture needles comprising a tungsten alloy such that the needle blanks or needles are curved, wherein the needles or needle blanks comprise tungsten alloy;
   then heating the needle blanks or suture needles from room temperature to a temperature below the recrystallization temperature of the alloy, wherein said temperature is in the range of about 900° C. to about 1250° C.; and,
   cooling the needle blanks or needles to room temperature, thereby improving the bending strength and bending stiffness of the curved needle blanks or needles at room temperature.

2. The method of claim 1, wherein the tungsten alloy needle blanks or needle comprises at least one or more metals selected from the group consisting of rhenium, tantalum or molybdenum.

3. The method of claim 2, wherein the tungsten alloy needle blanks or needle comprises rhenium.

4. The method of claim 2, wherein the tungsten alloy needle blanks or needle is heated to a temperature ranging from about 900 to about 1150° C. in an inert or reducing atmosphere.

5. The method of claim 2, wherein the tungsten alloy needle blanks or needle is heated to a temperature of about 900° C. in an oxidizing atmosphere.

6. The method of claim 1, wherein the tungsten alloy needle blanks or needle comprises up to 30 weight percent rhenium, and the balance tungsten.

7. The method of claim 6, wherein the tungsten alloy needle blanks or needle comprises about 20 to about 26 weight percent rhenium, and the balance tungsten.

8. The method of claim 7, wherein the tungsten alloy needle blanks or needle is heated for about 0.5 hours between 900 to 1150° C.

9. The method of claim 7, wherein the tungsten alloy suture needle is subjected to curvature prior to heat treatment.

10. The method of claim 9, wherein the curved suture needle is heated to a temperature ranging from about 900° C. to about 1250° C. in an inert or reducing atmosphere.

11. A suture needle produced according to the process comprising (1) forming needle blanks comprising up to 30 weight percent rhenium, and the balance tungsten, into curved suture needles; and, (2) heating said suture needles from room temperature to a temperature ranging from about 900 to about 1250° C. in an inert or reducing atmosphere for about 0.01 to 1 hour; and, (3) cooling the suture needle to room temperature, wherein the curved needles have improved bending strength and bending stiffness at room temperature.

12. The suture needle of claim 11, further treated by the step of heating said needle to a temperature of about 900° C. in an oxidizing atmosphere for about 0.01 to 1 hour.

* * * * *